United States Patent [19]

Meyer et al.

[11] Patent Number: 5,919,432
[45] Date of Patent: Jul. 6, 1999

[54] POLYAMINATED LIGANDS AND METAL COMPLEXES THEREOF

[75] Inventors: Dominique Meyer, Saint-Maur; Olivier Rousseaux, Senlis; Michel Schaefer, Lagny; Christian Simonot, Paris, all of France

[73] Assignee: Guerbet S.A., Villepinte, France

[21] Appl. No.: 08/959,083

[22] Filed: Oct. 28, 1997

Related U.S. Application Data

[62] Division of application No. 08/808,568, Feb. 28, 1997, Pat. No. 5,712,389, which is a continuation of application No. 08/366,732, Dec. 30, 1994, abandoned.

[30] Foreign Application Priority Data

Dec. 30, 1993 [FR] France ................... 93 15 933

[51] Int. Cl.$^6$ ............... C07F 5/00; C07C 229/00; A61K 49/00
[52] U.S. Cl. ............ 424/9.365; 549/29; 549/200; 549/13; 548/300.1; 548/146; 548/215; 548/233; 548/250; 544/106; 544/242; 544/336; 562/564; 562/565; 546/304
[58] Field of Search ............... 424/9.365, 9.3, 424/9.44, 9.35; 514/492; 549/29, 13, 200; 548/146, 215, 233, 300.1, 250; 562/564, 565; 546/304

[56] References Cited

U.S. PATENT DOCUMENTS

| 4,647,447 | 3/1987 | Gries et al. ................... 424/9 |
| 4,957,939 | 9/1990 | Gries et al. ................... 514/492 |
| 5,712,389 | 1/1998 | Meyer et al. .................. 540/465 |

FOREIGN PATENT DOCUMENTS

| 382583 | 8/1990 | European Pat. Off. . |
| 484989A1 | 5/1992 | European Pat. Off. . |
| 529645A1 | 3/1993 | European Pat. Off. . |
| 565930A1 | 10/1993 | European Pat. Off. . |
| 565930 | 10/1993 | Japan . |
| 89/12631 | 12/1989 | WIPO . |

*Primary Examiner*—Mukund J. Shah
*Assistant Examiner*—Pavanaram K. Sripada
*Attorney, Agent, or Firm*—Jacobson, Price, Holman & Stern PLLC

[57] ABSTRACT

Poly(amino acid) derivatives, which are chelating agents of paramagnetic metal ions, in which at least 3 of the donor nitrogen atoms carry identical or different substituents, of formula $$CH(R_1)\text{---}X,$$

in which X represents $CO_2R_a$, $CONR_bR_c$ or $P(R_d)O_2H$ and $R_a$, $R_b$ and $R_c$, which are identical or different, represent H or optionally hydroxylated $(C_1\text{--}C_8)$alkyl, $R_d$ represents OH, $(C_1\text{--}C_8)$alkyl or $(C_1\text{--}C_8)$alkoxy and $R_1$ represents a hydrophilic group with a molecular weight greater than 200 containing at least 3 oxygen atoms, with the proviso that at least 3 of the X groups are optionally salified acid functional groups.

10 Claims, No Drawings

POLYAMINATED LIGANDS AND METAL COMPLEXES THEREOF

This application is a division of 08/808,568 Feb. 28, 1997 U.S. Pat. No. 5,712,389 which is a continuation 08/366,732 Dec. 12, 1904 abandoned.

The invention relates to poly(amino acid) derivatives which can form chelates with paramagnetic metal cations as well as to these chelates, to the processes for preparing these compounds and to the compositions for medical imaging which contain these chelates.

In fact, these metal complexes modify the relaxation times of the protons excited by a radiofrequency in a magnetic field and are particularly useful as in vivo contrast agents for improving the images of the target organs obtained by nucleic magnetic resonance.

Gadolinium complexes, used in human clinical imaging, correspond to a spin-lattice or longitudinal relaxivity $R_1$ of between 3 and 5 mM$^{-1}$s$^{-1}$ in water at 37° C. for 20 MHz.

In order to improve the quality of the images, an increase is currently being witnessed in the doses, for example 0.3 mmol/kg of body weight in place of 0.1 mmol/kg, for conventional complexes containing a single Gd ion per molecule. This increase risks being accompanied by an increase in the side effects, especially those due to the osmolality of the complexes.

It would obviously be preferable to increase the intensity of the signal measured by increasing the relaxivity $R_1$ of the contrast agent.

It is known that $R_1$ is substantially increased when the metal chelate is grafted onto a macromolecule of biological or nonbiological origin, such as dextran, albumin or polylysine; nevertheless, if the relaxivity $R_1$ per gadolinium atom increases, the ratio of $R_1$ to the molecular weight of the coupled complex decreases so that the weight of a diagnostic dose unit increases, along with its cost.

The gadolinium complexes of the invention give relaxivities $R_1$ which are greater than those of the known complexes of analogous molecular weights; it is very likely, but without being restricted by this explanation, that the introduction of at least 3 hydrophilic side arms onto the acid groups, which are substituents of the donor nitrogen atoms of the known ligands, substantially decreases the freedom of movement of the paramagnetic complex and of the paramagnetic ion which is attached thereto, the rotation of which in the magnetic field is thus restricted.

The presence of side arms has sometimes been mentioned in certain patent applications, such as EP-A-299,795, EP-A-481,420 and WO 89/05802, but only by way of generalization of formulae, exemplified solely by molecules whose branchings are short, more or less hydrophobic and situated on at most two of the nitrogens, so that no favourable effect could be observed on the ratio of $R_1$ to the molecular weight and, obviously, no favourable effect has been suggested.

By correct selection of the side arms characteristic of the invention, it is possible, and this is another advantage, not only to improve the relaxivity of the complex but also to act on its biodistribution, for example by introducing into these arms fragments specific for certain biological receptors or alternatively by using arms of such a size that the molecular volume of the complex is sufficient to decrease its vascular permeability and that it remains in this region longer than current contrast agents.

According to a first aspect, the invention relates to compounds of poly(amino acid) type which can form chelates with paramagnetic metal ions, characterized in that at least 3 of the donor nitrogen atoms, namely those which will form coordination bonds with the metal ion, carry identical or different substituents of formula CH($R_1$)X, in which X represents $CO_2R_a$, $CONR_bR_c$ or $P(R_d)O_2H$ and $R_a$, $R_b$ and $R_c$ independently represent H or optionally hydroxylated ($C_1$–$C_8$)alkyl and Rd represents OH, ($C_1$–$C_8$)-alkyl or ($C_1$–$C_8$)alkoxy, and $R_1$ represents a hydrophilic group with a molecular weight greater than 200 containing at least 3 oxygen atoms, with the proviso that at least 3 of the X groups are optionally salified acid functional groups.

$R_1$ may contain nitrogen atoms but none can be a donor atom of the chelate, that is to say can form a coordination bond with the metal ion.

The majority of ligands known for complexing paramagnetic cations such as $Fe^{3+}$, $Mn^{2+}$, $Gd^{3+}$, $Dy^{3+}$ or even radioactive elements such as yttrium or technetium contain at least 3 nitrogen atoms substituted by an acetic, methylenephosphonic or phosphoric group, but the molecules of the present invention are differentiated therefrom by the presence on these 3 substituting groups of a functionalized hydrophilic side arm. These arms, or branchings, can be very varied in structure but they must be sufficiently hindering and must contain atoms capable of forming bonds in vivo with the surrounding medium such that these molecular interactions immobilize the molecule in the medium at least 3 points.

Thus, the replacement in molecules known for complexing paramagnetic metal ions of the substituents of at least 2 of the donor nitrogen atoms by 3, or better 4, preferably identical groups CH($R_1$)—X as defined in the specification makes it possible to obtain compounds according to the invention.

Mention may for example be made, among these known molecules, of those described in EP-A-232,751, EP-A-255,471, EP-A-287,465, EP-A-365,412, EP-A-391,766, EP-A-438,206, EP-A-484,989, EP-A-499,501, WO-89/01476, WO-89/10645 and WO-91/11475, as well as of the gadopentate and gadoterate ligands.

Some among the suitable $R_1$ groups contain only C, H and O atoms; these are especially poly[oxy($C_2$–$C_3$)-alkylenes], polyhydroxyalkyls or oligosaccharide or polysaccharide residues which are monofunctionalized in order to make it possible to link them to the carbon atom in the alpha position with respect to X.

$R_1$ can also represent more complex groups and especially

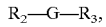

$$R_2—G—R_3,$$

in which $R_2$ represents nothing, alkylene, alkoxyalkylene, polyalkoxyalkylene, alkylene interrupted by phenylene, phenylene or a saturated or unsaturated heterocyclic residue, G represents an O, CO, OCO, COO, $SO_3$, $OSO_2$, CONR', NR'CO, NR'COO, OCONR', NR', NR'CS, CSNR', $SO_2NR'$, $NR'SO_2$, NR'CSO, OCSNR', NR'CSNR', P(O) (OH)NR' or NR'P (O) (OH) functional group, in which R' is H, ($C_1$–$C_8$) alkyl or $R_3$, $R_3$ represents alkyl, phenyl, alkyl substituted or interrupted by one or more groups selected from phenyl, alkyleneoxy, amino or amido substituted or unsubstituted by alkyl optionally substituted or interrupted by one of the above groups or $R_3$ is the residue of an optionally mono-functionalized compound selected from saccharides, oligosaccharides, peptides, biocompatible natural or synthetic macromolecules or molecules capable of being bound to an endogenous bioreceptor, as well as the salts of these compounds with physiologically acceptable acids or bases.

Preference is given to the compounds in which G is an amido group; CONR' or NR'CO, R' being H, $(C_1-C_8)$alkyl or $R_3$, or is the oxygen atom, forming an ether functional group with $R_2$ and $R_3$, and to those in which X is $CO_2H$.

Among these, the compounds in which the identical or different $R_1$ groups represent $R_2$—G—$R_3$ are particularly preferred when $R_2$ represents $(C_0-C6)$alkylene optionally interrupted by phenylene and $R_3$ represents $(C_1-C_{14})$alkyl optionally substituted or interrupted by one or more groups selected from phenyl, $(C_1-C_6)$alkoxy, amino and amido substituted or unsubstituted by alkyl or alkoxyalkyl, saccharides, oligosaccharides and biocompatible macromolecules such as polyethylene glycol and its $(C_1-C_2)$ ethers and dextran.

Mention may be made, as preferred $R_2$, of $(CH_2)_n$, $CH_2CHOH$, $CH_2CHOHCH_2$, $(CH_2)_4CHOH$, $(CH_2)_nC_6H_4$ or $C_6H_4$ with n=1, 2 or 3.

Throughout the present specification, except when otherwise mentioned, poly[oxy$(C_2-C_3)$alkylene] refers to polyoxyethylenes and polyoxypropylenes, especially polyethylene glycol and its $(C_1-C_3)$ monoesters and monoethers, with a molecular weight of less than 150,000; saccharides refers to carbohydrates such as mannose, fucose or galactose and aminosaccharides such as glucosamine or galactosamine; oligosaccharides refers to linear or cyclic chains containing 2 to 10 saccharide units, such as sucrose, maltotriose and cyclodextrins; polysaccharide refers to especially cellulose derivatives or hydroxyethyl starch, inulin or dextrans with a molecular weight of less than 20,000 or even greater for water-insoluble complexes; poly(hydroxyalkyl) refers to polyols with a molecular weight of less than 20,000 and especially poly(vinyl alcohol).

The alkyl, alkylene or alkoxy groups are, except when otherwise mentioned, linear, branched or cyclic $(C_1-C_{14})$ groups; these groups may be hydroxylated on one or several carbon atoms.

The phenyl, phenylene and heterocyclic groups may be substituted by OH, Cl, Br, I, $(C_1-C8)$alkyl, $(C_1-C_8)$-alkoxy, $NO_2$, $NR_xR_y$, $NR_xCOR_y$, $CONR_xR_y$ or $COOR_x$, $R_x$ and $R_y$ being H or $(C_1-C_8)$alkyl.

Mention may be made, among the aromatic, unsaturated or acyclic heterocyclic groups, of those derived from thiophene, furan, pyran, pyrrole, pyrrolidine, morpholine, piperazine, imidazole, pyridine, pyrimidine, pyrazine, pyridazine, thiazole, oxazole, pyrrolidine, imidazoline, dioxan, tetrazole, benzofuran, indole, quinoline and more or less saturated derivates or isomers.

Mention may be made, among the biocompatible natural or synthetic macromolecules, of polyoxy$(C_2-C_3)$-alkylenes or polyethers, polysaccharides, poly(amino acid)s, such as polylysine, proteins such as albumin or antibodies and their fragments, glycoproteins as well as oligomers or starburst polymers such as the dendrimers and arborols described in Angew. Chemie, Int. Ed., 29(2), 138–175, 1990 and EP-A-115,771.

It is also possible, especially when the chelates are intended to be administered to man orally or rectally, to use macromolecules which are insoluble or slightly soluble in water, such as the derivatives of poly(methacrylic acid)s or polyvinylpyrrolidone.

Mention may be made, among molecules capable of binding to an endogenous bioreceptor and thus making it possible to localize the chelate in an organ or in part of it, of those mentioned in U.S. Pat. No. 4,647,447 and especially hormones such as insulin, prostaglandins, steroids, antibodies, especially those specific for tumour cells, lipids or certain sugars such as arabinogalactan or glucose, or glycoproteins without end sialic acid known for their hepatic binding.

Moreover, the presence of a hydrophobic region on $R_1$, and especially that of a phenyl ring, can promote the formation of non-covalent bonds with the biological proteins and especially with albumin; this hydrophobic region can also be grafted onto another part of the poly(amino acid).

Monofunctionalized (poly)saccharide refers to a (poly) saccharide in which one of the saccharide units at the end of the chain has been modified to allow the formation of the G—$R_3$ or CH—$R_1$ bond; such a functionalization, described for instance in J. Polymer. Sc., Part A, Polymer Chemistry, 23, 1395–1405 (1985) and 29, 1271–1279 (1991) and in Bioconjugate Chem., 3, 154–159 (1992), is produced by reductive amination with $NH_3$ or an amine containing a reactive group or precursor of a reactive group or by oxidation through a lactone. It is thus possible to obtain a derivative having, as end functional group, a primary amine or a derivative carrying a reactive group, such as

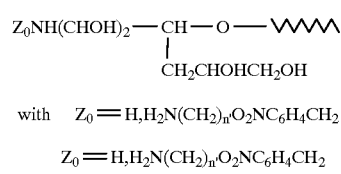

with $Z_0 = H, H_2N(CH_2)_{n'}O_2NC_6H_4CH_2$ $Z_0 = H, H_2N(CH_2)_{n'}O_2NC_6H_4CH_2$ or a derivative containing an acid functional group

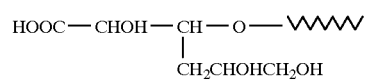

from maltose
whereas, for dextran,

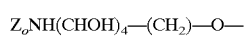

will be obtained.

Monofunctionalized polyethylene glycol or monofunctionalized polyethylene glycol ether refers to the compound in which one of the end groups carries a reactive functional group, such as those described in JMS Res. Macromol. Chem. Phys. C., 25(3), 325–373 (1985); reference may also be made to J. Org. Chem., 45, 5364 (1980) for the preparation of an aminopoly(ethylene glycol) or to Makromol. Chem., 182, 1379–1384 (1981) for various methods of substitution.

A preferred group of ligands of the invention is of formula

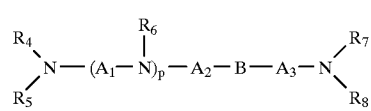

I in which

—$A_1$, $A_2$ and $A_3$, independently of one another, represent

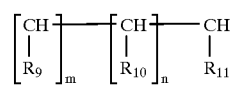

m and n being identical or different integers from 0 to 5, the sum of which has a value 1 to 5.

$R_9$, $R_{10}$ and $R_{11}$ independently represent H, alkyl, alkoxyalkyl, phenyl or phenylalkylene, and $R_{10}$ may additionally represent OH or alkoxy or one of the $R_9$ and $R_{11}$ groups from $A_1$, $A_2$ and $A_3$ represents the formula

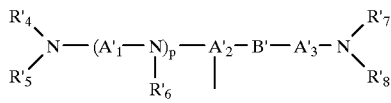

I' in which the letters can have the meanings of the letters with the same index number of the formula I, with the exception of one of the $R'_9$ and $R'_{11}$ groups which represents $(C_1-C_8)$ alkylene, optionally substituted by one or more $(C_1-C_8)$ alkoxy, the other not being I';

p is an integer from 0 to 5;

$R_4$, $R_5$, $R_6$, $R_7$ and $R_8$ independently represent H, alkyl, alkoxyalkyl, amidoalkyl substituted or unsubstituted by alkyl or alkoxyalkyl or $CH(R_{12})X$, $R_{12}$ being H, alkyl, alkoxyalkyl or $R_1$, or the $R_4$ and $R_7$ groups are bonded and taken together represent

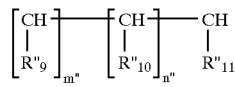

$R''_9$, $R''_{10}$, $R''_{11}$, m" and n" can have the meanings of the letters with the same index number in the formula I;

B is O or N—W and W represents the same groups as $R_5$ or polyoxy$(C_2-C_3)$alkylene, $(C_1-C_6)$alkylene-Y or Y, Y being a saturated or unsaturated heterocycle constituted of 1 or 2 fused rings, optionally substituted by one or several OH, alkyl, alkoxy or alkoxyalkyl groups, having up to 12 ring members, containing 1 to 4 heteroatoms selected from O, N and S, provided that when W represents Y, the carbon atom bonded to N is bonded to 2 carbon atoms of the heterocycle, or W represents the formula

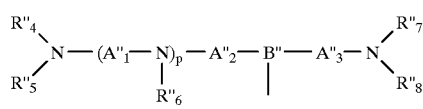

I"

in which the letters can have the meanings of the letters with the same index number in the formula I, with the exception of $R''_9$ and $R''_{11}$ which cannot represent I' and of B" which represents N—Q, Q being $(C_1-C_8)$alkylene optionally substituted by one or more alkoxy, or $A_2$—B—$A_3$ represents a heterocyclic group in which B is a saturated or unsaturated heterocycle with 5 or 6 ring members containing 1 or 2 heteroatoms selected from O, S and N, and $A_2$ and $A_3$ represent a group CH—$R_8$ in which $R_8$ is H or $(C_1-C_6)$alkyl, with the proviso that at least 3 groups from $R_4$, $R_5$, $R_6$, $R_7$, $R_8$ and W represent $CH(R_1)X$.

Compounds of formula I which contain 3 different nitrogen atoms substituted by at least one group $CH(R_1)X$, and more preferably by identical $CH(R_1)X$ groups, with $X=CO_2H$, are preferred for complexing lanthanide ions.

A first set of preferred ligands from those of formula I consists of the macrocycles of formula

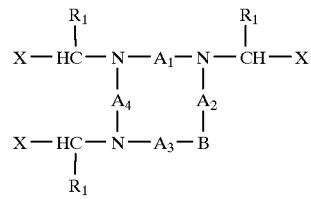

II in which the $R_1$ groups are preferably identical and the X groups preferably represent $CO_2H$, $A_1$ to $A_4$ independently represent

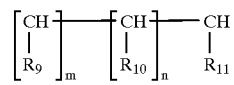

m and n being integers from 0 to 2, the sum of which has a value of 1 or 2, and $R_9$, $R_{10}$ and $R_{11}$ independently represent H, alkyl, alkoxyalkyl, phenyl or phenyl-alkylene, and $R_{10}$ may also represent OH or alkoxy, or one of the $R_9$ and $R_{11}$ groups represents the formula

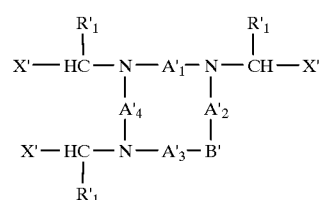

II' in which the letters can have the meanings of the letters with the same index number of the formula II, with the exception of $R'_9$ or $R'_{11}$ which is bonded to the macrocycle II and represents $(C_1-C_8)$alkylene, optionally substituted by alkoxy, B represents N—W and W represents the same as $R_5$ or H, alkyl, alkoxyalkyl, optionally substituted amidoalkyl, polyoxy$(C_2-C_3)$alkylene, these groups optionally containing a phenyl, $(C_1-C_6)$alkylene-Y or Y, Y being a saturated or unsaturated heterocycle constituted of 1 or 2 fused rings, optionally substituted by one or several OH, alkyl, alkoxy or alkoxyalkyl groups, having up to 12 ring members, containing 1 to 4 heteroatoms selected from O, N and S, provided that when W represents Y, the carbon atom bonded to N is bonded to 2 carbon atoms of the heterocycle, or, when $R_g$ and $R_{11}$ are different from the formula II', w represents this formula, in which the letters can have the meanings of the letters with the same index number of the formula II, with the exception of B' which represents N-$(C_1-C_8)$alkylene optionally substituted by alkoxy, or alternatively W represents $CH(R_1)X$, or $A_2$—B—$A_3$ represents a heterocyclic group in which B is a saturated or unsaturated heterocycle with 5 or 6 ring members containing 1 or 2 heteroatoms selected from O, S and N, and $A_2$ and $A_3$ represent a group CH—Re in which Re is H or $(C_1-C_6)$alkyl.

Preference is given to the macrocycles in which $A_1$ to $A_4$ represent $(CH_2)_2$ or $(CH_2)_3$ or one of them is substituted by $R_{11}$, $R_{11}$ representing alkyl, phenyl or phenylalkylene, preferably benzyl, optionally substituted, and more preferably those in which B is N—W.

Mention may be made, as examples of such macrocycles, of

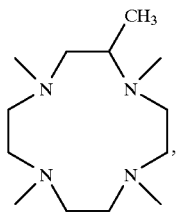,

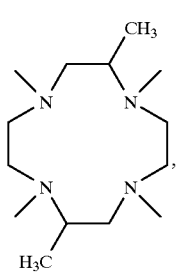,

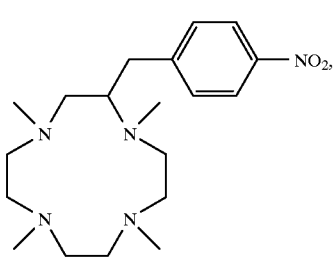,

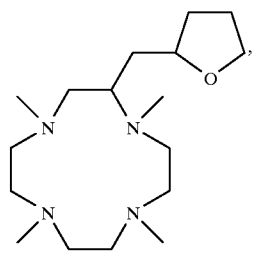,

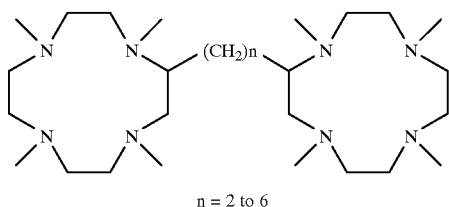

n = 2 to 6

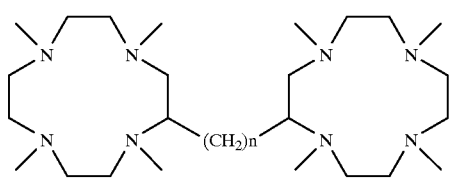

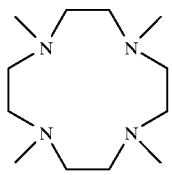

which are especially described in the references mentioned above.

In the case where a carbon atom of the macrocycle is substituted, it is especially preferable, in order not to obtain a mixture of isomers, for the 4 nitrogen atoms to be substituted by the same group $CH(R_1)COOH$.

Preference is given, among the derivatives of 1, 4, 7, 10-tetraazacyclododecane, to those of formula

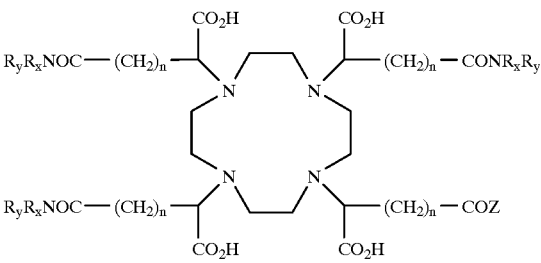

in which n is 2 or 3 and $R_x$ is H or optionally hydroxylated ($C_1$–$C_{14}$)alkyl and $R_y$ is hydroxylated ($C_2$–$C_{14}$)alkyl, polyoxy($C_2$–$C_3$) alkylene, polyhydroxyalkyl or the residue of an optionally monofunctionalized saccharide, oligosaccharide or polysaccharide; $R_y$ can also optionally comprise ($C_1$–$C_6$)alkylene or phenylene groups bonded to the above via amide or ether functional groups, and Z represents $NR_xR_y$ or OH.

Mention may also be made, among the derivatives of formula II, of those of formula

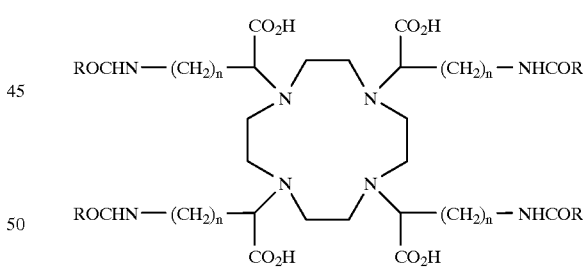

in which n is 2 or 3 and R represents hydroxylated ($C_2$–$C_{14}$) alkyl, polyoxy-($C_2$–$C_3$)alkylene or an optionally monofunctionalized saccharide, oligosaccharide or polysaccharide residue.

Another set of preferred ligands is that of the linear derivatives of formula

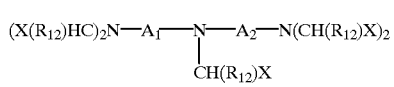

in which

A$_1$ and A$_2$ independently represent

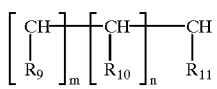

m and n being 0, 1 or 2 and their sum having the value 1 or 2, R$_9$, R$_{10}$ and R$_{11}$ independently representing H, alkyl, alkoxyalkyl, phenyl or phenylalkylene, and R$_{10}$ may also represent OH or alkoxy, or one of the R$_9$ and R$_{11}$ groups represents the formula

III' in which the letters can have the meanings of the letters with the same index number of the formula III, with the exception of R'$_9$ and R'$_{11}$ which cannot represent III' and one of which represents (C$_1$–C$_8$)alkylene optionally carrying one or more alkoxy, R$_{12}$ represents H, alkyl, alkoxyalkyl or R$_1$, provided that at least 3 CH(R$_{12}$)X groups represent CH(R$_1$)X and are preferably identical with X being CO$_2$H.

According to a second aspect, the invention relates to the paramagnetic complexes formed between the ligands of the invention and the suitable paramagnetic metal ions, such as those of gadolinium, dysprosium and manganese, as well as to the contrast agent compositions for medical imaging by nucleic magnetic resonance which comprise these complexes in combination with the usual vehicles and additives.

The ligands according to the invention can also form complexes with radioelements such as $^{99m}$Tc or $^{90}$Y, which can be used for performing a diagnosis or for carrying out a therapeutic treatment.

These complexes generally are internal salts, resulting from the neutralization by the central metal cation of acid groups of the ligand; when the complex comprises other acid groups, the latter may be salified by a pharmaceutically acceptable inorganic or organic base, including amino acids, for example NaOH, lysine, N-methylglucamine, arginine, ornithine or diethanolamine.

The doses at which the contrast agents according to the invention can be administered depend on the nature of the complex, on the relaxivity which it induces, on the administration route and on the targeted organ. For example, it is possible, by the oral route, especially for the gastrointestinal sphere, to administer from 0.1 to 2 mM/kg and parenterally from 0.001 to 1 mM/kg.

According to another aspect, the invention relates to a process for the preparation of the chelating poly(amino acid) derivatives which consists in reacting, with the polyamine which constitutes the skeleton thereof, a nucleophilic reactant of formula

in which Z' represents a halogen or a sulphonate and the reactive groups of R$_1$ and X are optionally protected, in order to obtain the substituted nitrogen atoms in accordance with the invention, optionally after deprotection of the reactive groups such as the hydroxyl and acid groups.

As in conventional nucleophilic substitutions, the reaction can be carried out in a polar or nonpolar aprotic solvent such as acetonitrile, dimethylformamide or toluene or in water or a pure or aqueous alcohol in the presence of an inorganic base, such as an alkali metal or alkaline-earth metal hydroxide or carbonate, or a tertiary amine, at a temperature between room temperature and the reflux temperature of the solvent.

When the nitrogen atoms of the polyamine do not all carry identical CH(R$_1$)X substituents, it is possible to carry out successive selective N-alkylations.

For example, in the case of 1,4,7,10-tetraazacyclododecane, it is possible to carry out a monoalkylation by reacting a marked excess of the macrocycle with Z'CH(R$_1$)X under suitably chosen operating conditions, as described in J. Org. Chem., 58, 3869–3876 (1993), or by blocking 3 of the N atoms by reacting with ethyl orthocarbonate or with a dimethylformamide acetal, as described in J. Chem. Soc. Chem. Comm., 1317–18 (1991); when hydrolysis is carried out of the compound obtained without having substituted the non-blocked N atom, a monoformamide is obtained and trialkylation of the other 3 N atoms can be carried out.

It is also possible to obtain unsymmetrical compounds by a suitable choice of the reactants leading to the preparation of the polyamine skeleton; examples of these reactions are given in EP-299,795, for the preparation of linear or cyclic derivatives.

In the case of certain R$_1$ substituents, especially those of formula R$_2$—G—R$_3$ in which R$_3$ is a macromolecule and G is an amido group, it is advantageous to prepare the derivatives according to the invention via compounds of formula I in which the nitrogen atoms carry substituents of formula CH(R'$_1$)X, R'$_1$ being of low molecular weight, containing about 2 to 5 carbon atoms.

These chemical intermediates are another subject-matter of the invention.

These compounds are represented by the formulae I, II and III, for which the meanings of the letters are identical to those mentioned above, with the exception of that of CH(R$_1$)X which is CH(R$_2$—G')X', G' being a reactive functional group which is a precursor of G, such as COOR', SO$_3$R', PO$_3$R', NHR', SO$_2$NHR', N=C=S, N=C=O and OH and X' representing X or protected X, especially an ester group.

Precursor group of G means any functional group which is known to allow the formation of a covalent bond under operating conditions which are accessible in industry and, for example, in addition to the above groups, those used for graftings onto proteins.

These derivatives can be prepared as described above for the derivatives of the invention of formula I, but with nucleophilic reactants Z'CH(R$_2$G')X'.

The coupling of these intermediates to the reactive derivatives of R$_3$ to give the ligands according to the invention, in which at least 3 N atoms carry a substituent CH(R$_2$—G—R$_3$)X, can be carried out according to conventional methods, especially those commonly employed in peptide syntheses, or alternatively after activation of the acids as acid halides or anhydrides or in the presence of a dehydrating agent such as carbodiimides; depending on the nature of G' and of the reactive group of R'$_3$, an amine alkylation or acylation or the condensation of an aldehyde with an amine followed by a reduction may be carried out.

Mention may be made, among these chemical intermediates, of those of formula

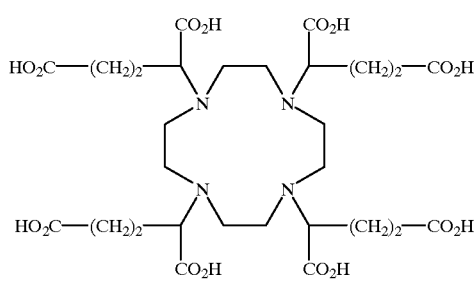

and of the derivatives of formula

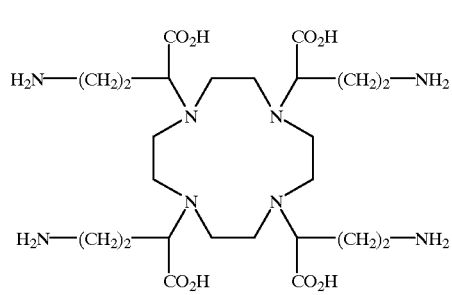

and of their alkyl esters or salts.

The compounds of formula VI are particularly advantageous in that they make it possible to obtain tri- or tetraamides derived from the carboxyl groups on the C in the γ position with respect to the nitrogen without modification of the CO$_2$H groups in the a position, when the amidification reaction is carried out by reaction of a chelate of VI with an amine in the presence of a dehydrating agent such as a carbodiimide in aqueous or organic medium.

Depending on the operating conditions, relative proportions of reactants, solvent, reaction time and temperature, and the reactivity of the amine used, a compound of formula VIII or IX, or their mixtures, is obtained.

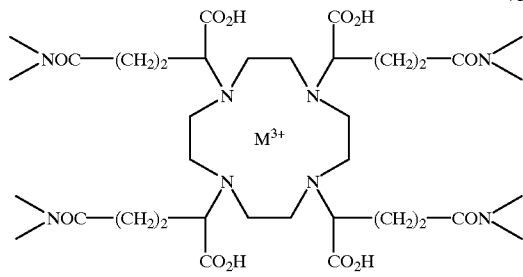

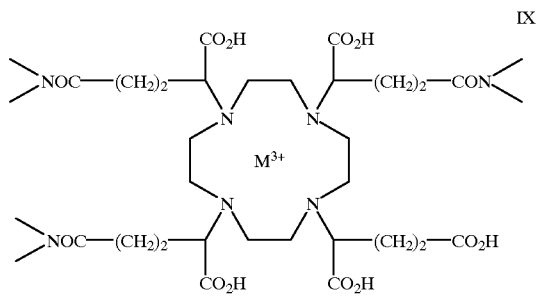

in which $M^{3+}$ is preferably $Gd^{3+}$, which makes it possible directly to obtain the complex which is useful as contrast agent, but $M^{3+}$ could be any cation chelated by the ligand of formula VI; $M^{3+}$ should then be separated from the ligands VIII or IX by the action of an acid such as HCl, H$_2$S or HCN, the ligands then being reacted with an oxide or a salt of the paramagnetic element to be complexed.

It is obvious that this process can be applied, for the preparation of amides, to other compounds in which the side arm contains an acid functional group and X is CO$_2$H or PO$_3$H.

In fact, it makes possible the selective protection of the various acids and amines involved in the coordination of the metal.

The metal complexes of the derivatives of formula I, and those of the synthetic intermediates of formula VI, can be prepared conventionally by reacting one equivalent of the oxide or of a salt of the metal in aqueous medium, preferably at a temperature greater than 20° C. but less than 90° C.

In the following text, a description is given of examples of the preparation of intermediates and of ligands or chelates according to the invention.

EXAMPLES
Example 1
Preparation of the compound of formula

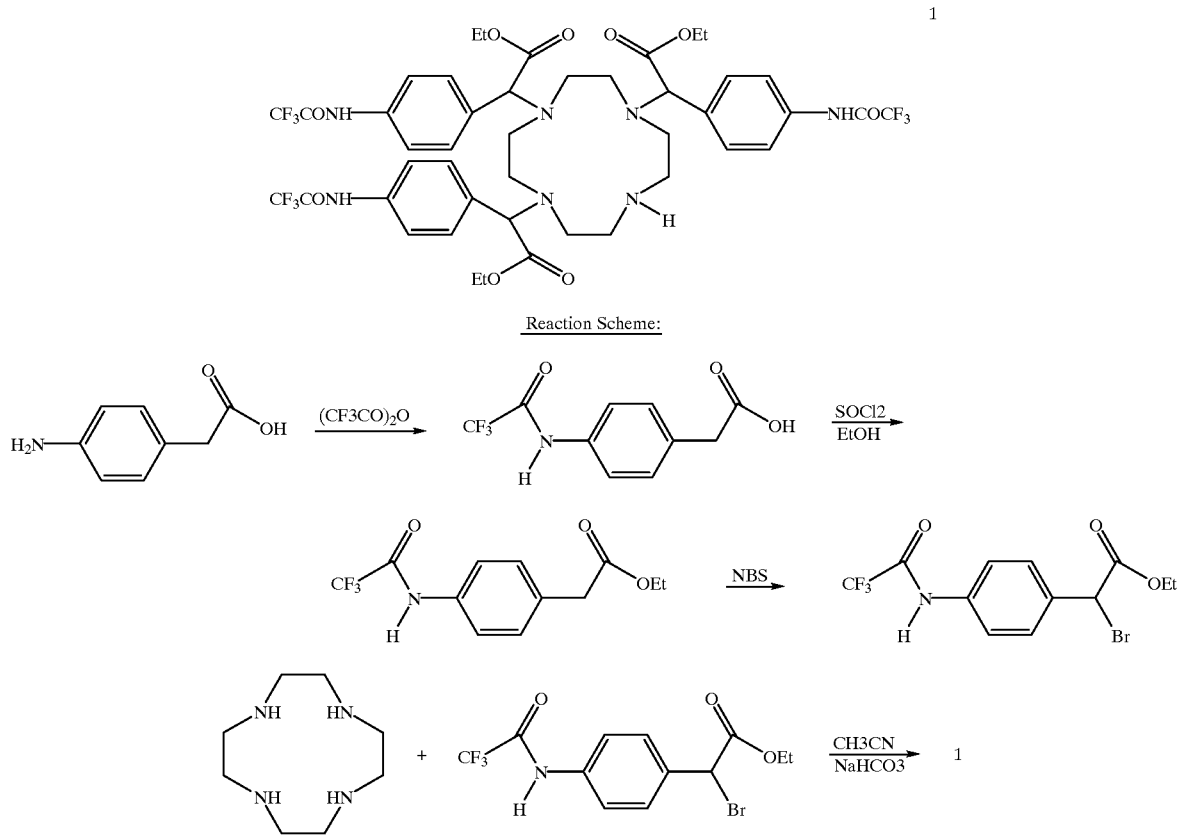

Reaction Scheme:

1. 4-(Trifluoroacetamido)benzeneacetic acid

This compound is prepared according to the method described by K. D. Janda et al. (J. Am. Chem. Soc., 113, No. 1, p. 291 (1991)) with a yield of 75%.

10 g of 4-aminophenylacetic acid give 12 g of a trifluoroacetylated derivative characterized by $^1$H NMR δ ppm (DMSO): 7.45 (d, 4H), 7.56 (s, 2H), 11.15 (s, 1H).

2. Ethyl 4-(trifluoroacetamido)benzeneacetate

This compound is obtained, starting from the acid prepared above according to the method described by K. D. Janda (J.A.C.S., 113, No. 1, p. 291 (1991)), with a yield of 33%. 12 g of acid are converted to 4.4 g of ester, which are characterized by $^1$H NMR (δ ppm) DMSO: 1.1 (t, 3H), 3.6 (s, 2H), 4.05 (q, 2H), 7.4 (q, 4H).

3. Ethyl α-bromo-4-(trifluoroacetamido)benzene-acetate 4 g (14.5 mmol) of the ester prepared above are suspended in $CCl_4$ (150 cm$^3$). The mixture is stirred and brought to a gentle reflux. 2.8 g of N-bromosuccinimide and 0.2 cm$^3$ of concentrated hydrobromic acid solution (38%) are introduced into the reactor and the medium is stirred under reflux for 48 h. The insoluble material is filtered off and the solvent is evaporated. The residue is purified through silica (eluent $CH_2Cl_2$) to lead to 2 g of purified product.

Yield: 40% $^1$H NMR (δ ppm): 1.2 (t, 3H), 4.1 (q, 2H), 5.9 (s, 1H), 7.6–7.8 (m, 4H), 11.4 (s, 1H).

4. Preparation of Compound 1

120 mg of $NaHCO_3$ and 500 mg of the brominated derivative prepared above are added to a solution of 60 mg (0.35 mmol) of 1,4,7,10-tetraazacyclododecane in 10 cm$^3$ of acetonitrile. The suspension is stirred at a temperature of 40° C. for 48 h. The reaction medium is then filtered and the solvent evaporated under reduced pressure. The residue is taken up in isopropyl ether to give 600 mg of crude product in powder form. The product is purified by chromatography on a silica column (eluent:AcOEt/MeOH 90/10 then 80/20).

Weight obtained: 110 mg Yield: 32% $^{13}$C NMR (δ ppm) CDCl$_3$: 14.6, 61.7, 63–67, 116 (CF$_3$), 130.6–136 (aromatic C atoms), 155 (CONH), 172 (CO).

The amine functional groups of Compound 1 are then deprotected by reaction with $NaBE_4$ in ethanol, as described in Chem. Ber., 103, 2437 (1970).

An intermediate of the invention, for which $R_2=C_6H_4$ and G' is $NH_2$, is thus obtained, which is the precursor of a compound which contains 3 substituents, according to the invention.

Example 2

Preparation of the compound of formula 2

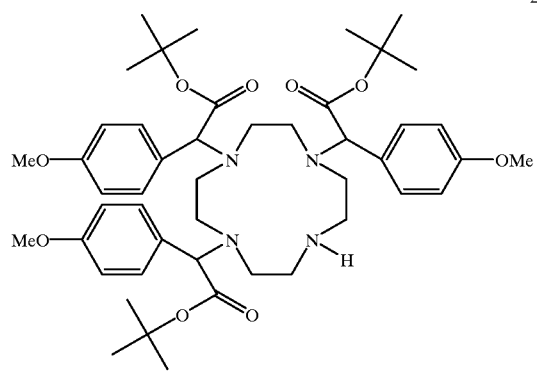

Reaction scheme

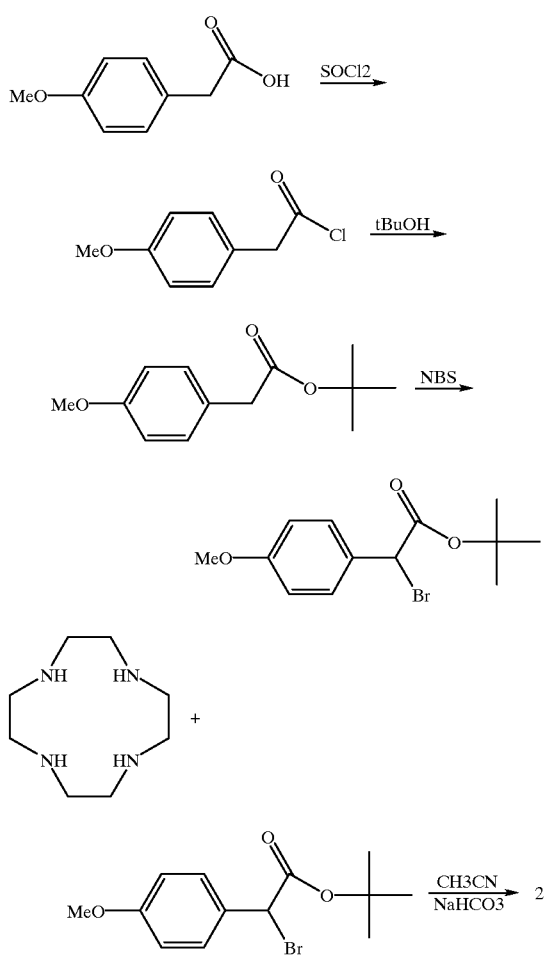

1. t-Butyl Para-methoxyphenylacetate

The product is prepared according to the method described by H. Gotthardt et al. (Chem. Ber. 109, p. 740 (1976)) and P. G. Mattingly (J. Org. Chem., 46, p. 1557 (1981)). 5 g of t-butyl ester are obtained from 15 g of para-methoxyphenylacetic acid.

Yield: 28% $^1$H NMR (δ ppm): 1.3 (s, 9H), 3.46 (s, 2H), 3.75 (s, 3H), 6.8–7.3 (q, 5H).

2. t-Butyl α-bromo-para-methoxyphenylacetate

The product is prepared according to the method described by H. Gotthardt et al. and P. G. Mattingly.

5 g of the t-butyl ester prepared above lead to is 2.5 g of brominated derivative. Yield: 33% $^1$H NMR (δ ppm): 1.48 (s, 9H), 3.82 (s, 3H), 5.28 (s, 3H), 6.83–7.6 (m, 5H).

3. Preparation of Compound 2

600 mg of $NaHCO_3$ are added to a solution consisting of 285 mg of 1,4,7,10-tetraazacyclododecane (1.65 mmol) in 30 cm$^3$ of acetonitrile with stirring. 2 g of the α-brominated ester prepared above are introduced into the suspension and the reaction medium is stirred for 48 h at room temperature. After filtration and evaporation of the solvent, the residue is purified by chromatography on silica (eluent: $CH_2Cl_2$/AcOEt/MeOH 80/10/4) to lead to 500 mg of purified product.

Mass spectrum (FAB$^+$): peak 833 $^{13}$C NMR (δ ppm): 27.6 ($CH_3$ t-butyl), 45–50 (ring), 54.9 ($CH_3O$), 61.1 (t-butyl), 68 (NCH), 113.6–127.2–130.4 –158 (aromatic C atoms), 171 (C=O).

The phenol functional groups of Compound 2 are then deprotected by reaction with boron tribromide, as described in Org. Synth. Coll. Vol. V, 412 (1973) or in J. Org. Chem., 44, 4444 (1979).

An intermediate of the invention, for which $R_2=C_6H_4$ and G' is OH, is thus obtained, which can be conventionally substituted.

Example 3

Preparation of the compound of formula 3

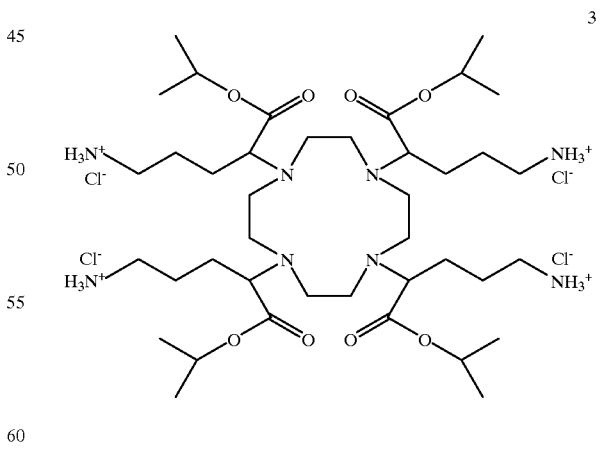

of the corresponding acid and of the complex with Gd$^{3+}$.

Reaction Scheme

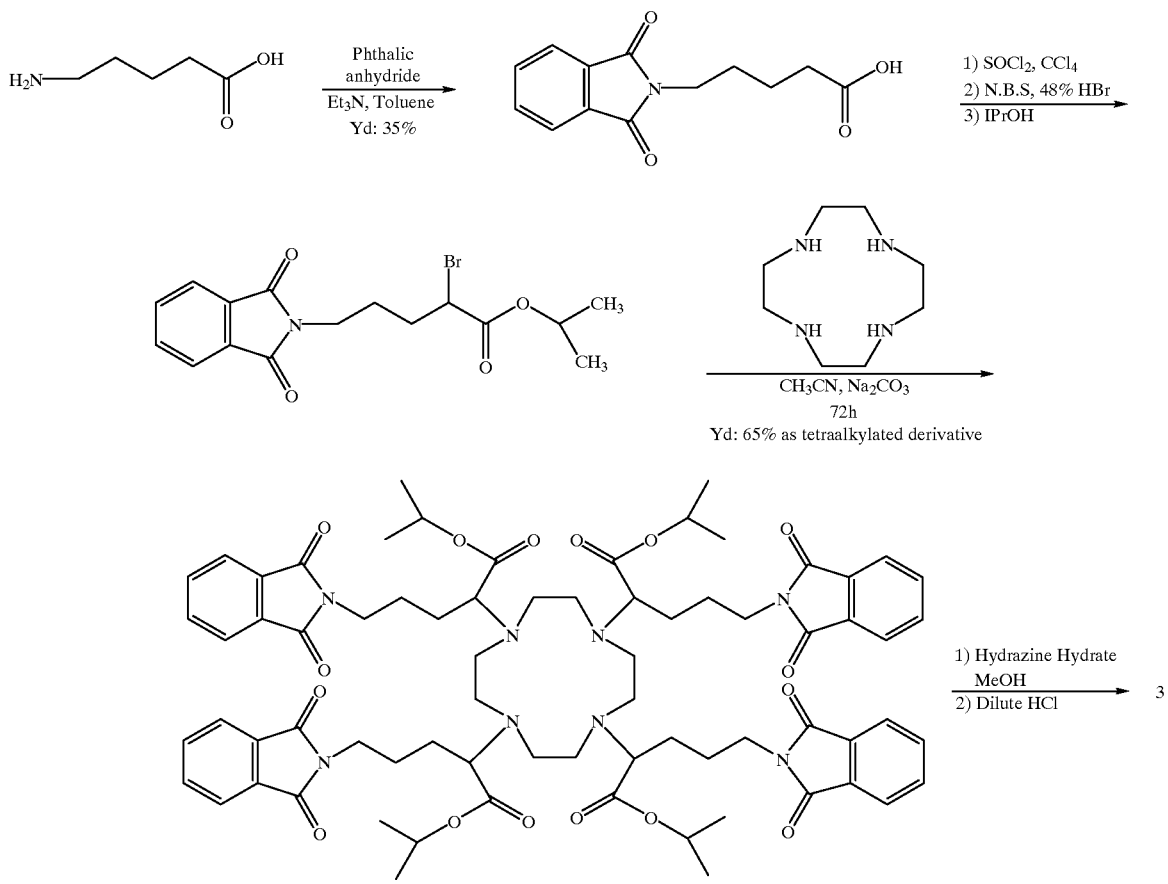

1. 5-(N-Phthalimido)pentanoic acid

12.6 g (85.1 mmol) of phthalic anhydride, 10 g (85.1 mmol) of 5-aminovaleric acid, 1.2 ml (8.51 mmol) of triethylamine and 130 ml of toluene are mixed and stirred at reflux for 1 h in a three-necked flask equipped with a Dean and Stark apparatus for removing the water formed by azeotropic distillation. After one night at room temperature, the precipitate formed is filtered and washed with heptane, then with 200 ml of a 1N hydrochloric acid solution and then with 100 ml of water. After drying, 7.37 g of 5-(N-phthalimido)pentanoic acid are obtained in the form of white crystals with a yield of 35% (M.p.=115° C.). $^1$H NMR (CDCl$_3$) δ (ppm): 7.8 (m, 2H), 7.7 (m, 2H), 3.7 (t, 2H), 2.4 (t, 2H), 1.7 (m, 4H). $^{13}$C NMR (CDCl$_3$) δ (ppm): 178, 168, 134, 133.9, 123.2, 37.4, 33.3, 27.9, 21.8.

2. Isopropyl ester of 2-bromo-5-(N-phthalimido)-pentanoic acid

7.2 g (29.1 mmol) of 5-(N-phthalimido)pentanoic acid are added to a solution of 3 ml of carbon tetrachloride and 8.5 g (116 mmol) of thionyl chloride. The solution is brought to reflux for 1 hour; 14 ml of carbon tetrachloride, 6.2 g (34.9 mmol) of N-bromosuccinimide and 2 drops of 48% aqueous hydrobromic acid are added and the solution is left under reflux for 2 hours. The cooled solution is poured into 60 ml of isopropanol and stirred for 30 minutes. After evaporation under vacuum, the oil obtained is purified on silica, elution being carried out with a 50 dichloromethane/50 heptane mixture and then with dichloromethane. After evaporation of the solvents, 8.2 g of the isopropyl ester of 2-bromo-5-(N-phthalimido)pentanoic acid are obtained with a yield of 76.6% in the form of a pale-yellow oil which crystallizes (M.p.: 75° C.).

$^1$NMR (CDCl$_3$) δ (ppm): 7.85 (m, 2H), 7.7 (m, 2H), 5 (m, 1H), 4.2 (t, 1H), 3.7 (t, 2H), 1.7–2.2 (m, 4H), 1.2 (d, 3H), 1.25 (d, 3H). $^3$C NMR (CDCl$_3$) δ (ppm): 168.5, 168, 133.9, 132, 123.2, 69.7, 45.5, 36.9, 31.9, 26.9, 21.5, 21.3.

3. Tetraisopropyl ester of 1,4,7,10-tetraazacyclododecane-1.4,7,10-tetra[2-(5-N-phthalimido)-pentanoic] acid

0.92 g (5.34 mmol) of 1,4,7,10-tetraazacyclododecane, 11.8 g (32.1 mmol) of the compound (2), 3.4 g (32.1 mmol) of sodium carbonate and 36 ml of acetonitrile are stirred under reflux for 72 h. After filtration and evaporation under vacuum, the oil obtained is taken up in dichloromethane and washed with water. After drying and evaporation of the dichloromethane, the residue obtained is purified by two successive flash chromatographic operations on silica with, as first eluent, a 95 CH$_2$Cl$_2$/5 C$_3$OH mixture and then, as second eluent, 95 CH$_3$COOC$_2$H$_5$/5 H$_3$OH. After evaporation of the solvents, 4.62 g of the tetraisopropyl ester of 1,4,7,10-tetraazacyclododecane- 1,4,7,10-tetra[2-(5-N-phthalimido)pentanoic] acid are obtained with a yield of 65% in the form of amorphous crystals.

$^1$H NMR (CDCl$_3$) δ (ppm): 7.5–7.85 (m, 16H), 4.8–5.1 (m, 4H), 1–3.8 (m, 72H) $^{13}$C NMR (CDCl$_3$) δ (ppm): 167, 166.9, 162.8, 128.4, 126.9, 117.8, 62.2, 57.9, 45.3, 45, 32.5, 22.3, 20.4, 16.9, 16.7.

4. Tetrahydrochloride of the tetraisopropl ester of 1,4,7,10-tetraazacyclododecane-1,4,7,10-tetra[2-(5-amino)pentanoic] acid

1 g (0.76 mmol) of the tetraisopropyl ester of 1,4,7,10-tetraazacyclododecane-1,4,7,10-tetra[2-(5-N-phthalimido)pentanoic] acid, 0.15 ml of hydrazine hydrate (3.04 mmol) and 8 ml of methanol are stirred under reflux for 1 hour. 10 ml of 0.5M hydrochloric acid are added at room temperature. The precipitate formed is removed by filtration and the filtrate is evaporated.

5. 1,4,7,10-Tetraazacyclododecane-1,4,7,10-tetra[2-(5-amino)pentanoic] acid (hydrochloride)

3.1 g of the phthalimido derivative obtained according to 3 and 270 ml of a 6N aqueous HCl solution are maintained under reflux, with stirring, for several days; concentration is then carried out under reduced pressure to a volume of 20 ml, the solid is separated, extraction is carried out with ethyl ether and the extract is brought to dryness. The residue is purified by chromatography through silanized silica, elution being carried out with water; the aqueous solution of the desired product is concentrated and the residue is precipitated in ethanol, to give 1.15 g of the acid. M.p.=250° C.

$^1$H NMR (D$_2$O) δ ppm: 3.8–4 (m, 4H), 2.8–3.6 (m, 24H), 1.5–2.2 (m, 16H).

6. Complex of the above acid with Gd$^{3+}$ 1.2 g of the above product and 0.5 g of GdCl$_3$.6H$_2$O are dissolved in 17 ml of water. The pH of the medium changes with the reaction; it is maintained at 6 by addition of a 1N aqueous NaOH solution; when the pH has stabilized at 6, a fresh addition of NaOH brings it to 7 before concentration under reduced pressure. The solid obtained is precipitated in 75% (V/V) ethanol.

1.1 g of the desired product are thus obtained in the form of beige crystals which melt above 300° C.

Example 4

1,4,7,10-Tetrakis{3-[N-(2-hydroxyethyl)-N-(1-deoxyglucitol) carboxamido]-1-carboxypropyl}-1,4,7,10-tetraazacyclododecane (gadolinium complex, Na salt, Compound No. 4).

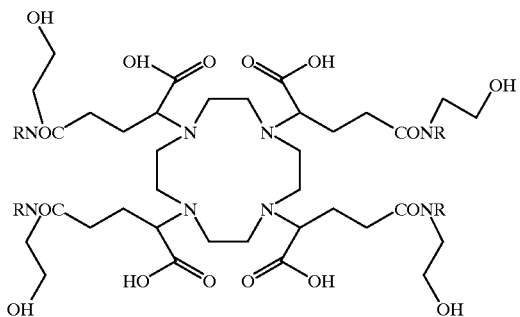

1. 1,4,7,10-Tetrakis[1,3-di(methoxycarbonyl)-propyl]-1,4,7,10-tetraazacyclododecane 43 g (0.18 mol) of dimethyl 2-bromoglutarate, prepared according to T. R. Hoye, J. Org. Chem., 1982, 47, 4152–4156, are added dropwise to a mixture of 4.3 g (0.025 mol) of 1,4,7,10-tetraazacyclododecane, 25 g (0.18 mol) of potassium carbonate and 100 ml of acetonitrile at 50° C. The suspension is stirred for 48 hours at this temperature and then filtered. After evaporation of the acetonitrile to dryness, the residue is purified twice by flash chromatography on silica with a dichloromethane/methanol gradient. After evaporation of the solvents, 15 g of beige powder are obtained with a yield of 75%.

TLC: SiO$_2$, CH$_2$Cl$_2$/CH$_3$OH (9/1), R$_f$=0.8.

2. 1,4,7,10-Tetrakis[1,3-dicarboxypropyl]-1,4,7,10-tetraazacyclododecane 15 g (0.019 mol) of the 1,4,7,10-tetrakis[1,3-di(methoxycarbonyl)propyl]-1,4,7,10-tetraazacyclododecane compound are stirred in 100 ml of methanol and 250 ml of N aqueous NaOH solution for 16 hours at room temperature. The octaacid in solution is purified by retention on IRA 458 resin, marketed by Rohm and Haas, and then elution with an acetic acid gradient. After evaporation of the solvents, 11 g of white powder are obtained with a yield of 85%.

TLC: SiO$_2$, CH$_3$COOC$_2$H$_5$/CH$_3$OH/CH$_3$COOH (35/35/40), R$_f$=0.2. $^{13}$C NMR DMSO (δ ppm): 31.13, 47.50, 61.13, 61.76, 172.29, 174.9. Mass spectrum (FAB$^+$): peak=693

3. Complex with gadolinium of the above intermediate (Na pentasalt)

A suspension of 12.1 g (0.0175 mol) of the compound obtained according to 2 and 6.5 g (0.0175 mol) of GdCl$_3$.6H$_2$O in 225 ml of water is brought to a pH of 6.5 by addition of a 1N aqueous NaOH solution and maintained at this pH by successive additions. When the pH no longer changes, the water is removed under reduced pressure to give 19.8 g of white powder, a mixture of the final product with NaCl.

4. Monosodium salt of the gadolinium complex of 1,4,7,10-tetrakis{3-[N-(2-hydroxyethyl)-N-(1-deoxyglucitol)carboxamido]-1-carboxypropyl}-1,4,7,10-tetraazacyclododecane (Compound No. 4)

A suspension of 2 g (2.9 mmol) of the compound obtained in 2 in 100 ml of water with 1.1 g (2.9 mmol) of gadolinium (III) chloride hexahydrate, at 80° C., has a sufficient amount of 0.1N aqueous NaOH solution added to it to give a pH of 4.3. The solution obtained is brought to a pH of 7 by addition of the same NaOH solution and is then concentrated to a volume of 10 ml. After addition of 2.8 g (12.2 mmol) of 1-deoxy-1-(2-hydroxyethylamino)-D-glucitol, the pH is brought to 5.3 by addition of 1N aqueous hydrochloric acid solution and 2.3 g (12.2 mmol) of 1-(3-dimethylaminopropyl)-3-ethylcarbodiimide hydrochloride are added and the solution is stirred for 16 hours at room temperature. The solution is brought to a pH of 3.5 by addition of IRN 77 resin, marketed by Rohm and Haas, filtered, adjusted to a pH of 5.5 using 0.1N aqueous NaOH solution and then eluted on silanized silica. Evaporation of the water, then washing the residue twice with 100 ml of ethanol and drying produces 4 g of white powder.

Example 5

Gadolinium complex of Compound No. 5 of formula

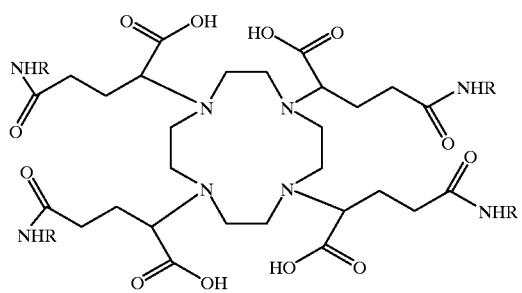

with

R = 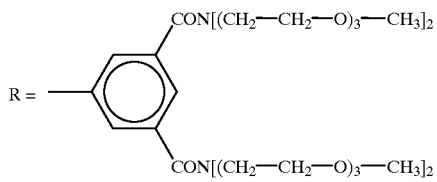

1. Preparation of R—NO$_2$ 1 g of 5-nitroisophthalic acid chloride is introduced at 0° C. into a solution of 2.5 g of bis(3,6,9-trioxadecyl)amine, prepared according to the method described in Tetrahedron, 47, 411 (1991), and 1.12 ml of triethylamine in 10 ml of dichloromethane. The medium is left stirring for 2 hours at room temperature and then washed with water, dried over Na$_2$SO$_4$ and concentrated. The residue obtained is purified by chromatography on silica, elution being carried out with a CH$_2$Cl$_2$/CH$_3$OH (95/5) mixture. 2.26 g of the desired product are thus obtained in the form of a yellow oil.

2. 5-Amino-N,N,N',N'-tetrakis(3,6,9-trioxadecyl)-1,3-benzenedicarboxamide (RNH$_2$)

2.2 g of the above nitro derivative in 10 ml of ethanol are hydrogenated in the presence of 10% Pd/C under pressure of 10$^5$ Pa at a temperature of 20° C. After filtration and concentration under reduced pressure of the medium, 2 g of the amine are obtained in the form of a yellow oil.

$^1$H NMR (CDCl$_3$) δ (ppm): 6.7 (s, 2H), 6.6 (s, 1H), 3.35–3.7 (m, 48H), 3.25 (s, 12H).

3. Complex of Compound No. 5 with Gd$^{3+}$ 1 g of the complex obtained in Stage 3 of Example 4, 3.23 g of RNH$_2$ and 6.8 g of 1-(3-dimethylaminopropyl)-3-ethylcarbodiimide (hydrochloride) are dissolved in 13 ml of water; the solution is left stirring for 48 hours at room temperature with several additions of a 1N aqueous HCl solution in order to maintain the pH about 7. The medium is brought to 150 ml by addition of water and then subjected to an ultrafiltration in a nova-type minisette cassette, marketed by Filtron (USA), with a membrane with a cut-off threshold of 3 Kdaltons.

The desired product has a retention time of 30 minutes, during gel filtration in a 60 cm×2 cm Pharmacia column filled with Superdex® 75 gel, with an eluent (H$_2$O) flow rate of 1 ml per minute.

Example 6

Complex with Gd$^{3+}$ of Compound No. 6 of formula (sodium salt)

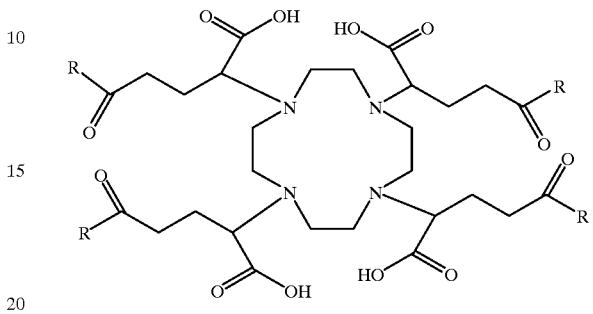

with R═HN(CH$_2$(CHOH)$_4$—CH$_2$OH)$_2$.

1 mmol of the complex obtained in Stage 3 of Example 4 and 4.6 mmol of commercial bis(2,3,4,5,6-pentahydroxyhexyl)amine are dissolved in 13 ml of water; the pH of the solution is brought to 6 by addition of a 2N aqueous HCl solution and then 21 mmol of 1-(3-dimethylaminopropyl)-3-ethylcarbodiimide hydrochloride are added; after stirring for 4 hours, 21 mmol of carbodiimide are again added to the medium; after stirring overnight, 100 ml of water are added and the solution is filtered through an IRN 77 resin, in the H$^+$ form, marketed by Rohm and Haas, and then through an IRA 458 resin in the OH$^-$ form, marketed by Rohm and Haas; the final solution is ultrafiltered in a Filtron cassette equipped with a membrane with a cut-off threshold of 1 Kdalton.

The final product has a retention time of 78 minutes in a gel filtration on Superdex® 30 with an eluent (phosphate buffer, pH=7.2) flow rate of 1 ml/minute.

Example 7

Complex with Gd$^{3+}$ of Compound No. 7 of formula

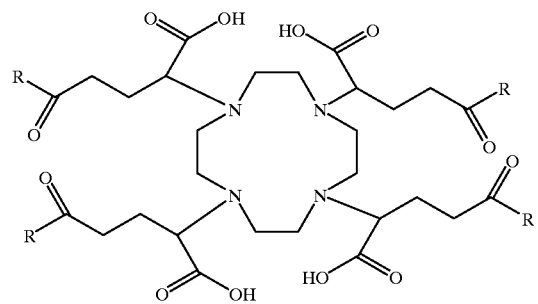

with

-continued

R = 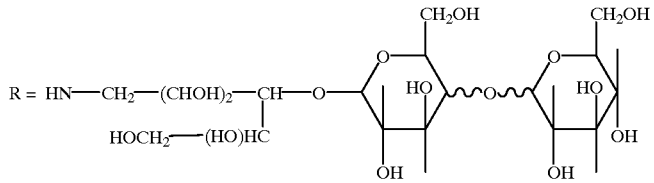

1. Preparation of $RCH_2C_6H_5$ and then RH according to J. Carbohydrate Chemistry, 11(7), 813–835 (1992)

8.2 ml of distilled benzylamine are introduced into a solution at 60° C. of 23.6 g of maltotriose in 16 ml of water. After stirring for 3 hours at this temperature, 60 ml of methanol are added and the medium is brought to 25° C. before adding 3.56 g of sodium borohydride portionwise.

After stirring for 48 hours at 20° C., the solution is concentrated and the residue dissolved in 100 ml of methanol; a 4N aqueous hydrochloric acid solution is added until a pH of 3 is reached and concentration is carried out after addition of two volumes of methanol. The residue is dissolved in 100 ml of methanol, filtration is carried out and the solution is then concentrated. The residual solid is washed with ethanol at 70° C. and then dried to give 25.6 g of $RCH_2C_6H_5$.HCl. The amine is obtained by the action of an IRA 458 resin, marketed by Rohm and Haas, and purified by passing through an IRN 77 resin. 17.7 g of solid are thus obtained. TLC (Merck 60 F silica) eluent:dioxane/water/ 25% aqueous $NH_3$ (w/V: 8/3/2) $R_f$=0.7

The benzylamine obtained is dissolved in 100 ml of water and a 25% aqueous $NH_4OH$ solution is added until pH 9. After addition of 4 g of Pd/C, the mixture is hydrogenated under a pressure of $6 \times 10^5$ Pa for 5 hours at 40° C. and for 12 hours at room temperature.

After filtration, the solvent is removed under reduced pressure and the oil is purified by passing through an IRN 77 resin, in the $H^+$ form. 10.9 g of the desired solid are obtained.

TLC (above conditions): $R_f$=0.2 $^3C$ NMR ($D_2O$): 40.6 ($CH_2$—$NH_2$), 57.7–59.5 ($CH_2OH$), 66.6–70.1 (CHOH), 74.1 and 79.2 (C—O), 97 and 97.6 (O—C—O).

2. Complex of Compound No. 7 with $Gd^{3+}$ 4.66 g of the product obtained above are introduced at 60° C. into 210 ml of dimethylformamide, followed by 1 g of the $Gd^{3+}$ complex obtained in Example 4 (3), 886 mg of 1-hydroxybenzotriazole, 1.25 g of 1-(3-dimethylaminopropyl)-3-ethylcarbodiimide hydrochloride and 0.9 ml of triethylamine. The medium is kept stirring for 5 hours at 60° C. and then for 48 hours at room temperature before concentrating under reduced pressure. The residue is triturated in $CH_2Cl_2$ and then purified by ultrafiltration through a Filtron mini-cassette with a membrane with a cut-off threshold of 1 Kdalton.

Example 8

Complex with $Gd^{3+}$ of Compound No. 8 of formula

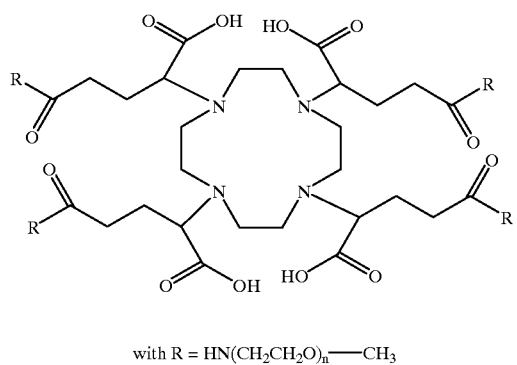

with R = $HN(CH_2CH_2O)_n$—$CH_3$

The methyl ether of aminopolyethylene glycol (MM≈5000) can be prepared according to one of the methods described above or bought commercially.

15 g of the amine are dissolved at 40° C. in 700 ml of dimethylformamide and a solution of 0.5 g of the $Gd^{3+}$ complex prepared in Example 4 (3) in 50 ml of water is added, followed by 0.48 g of hydroxybenzotriazole hydrate, 0.5 ml of triethylamine and 2.72 g of 1-(3-dimethylaminopropyl)-3-ethylcarbodiimide hydrochloride.

After stirring for 5 days at room temperature, the solution is concentrated under reduced pressure. The residue, dissolved in 150 ml of water, is ultrafiltered in a Filtron minicassette with a membrane with a cut-off threshold of 5 Kdaltons.

After lyophilization, 3.5 g of product, a mixture of triamide (one of the R groups=OH) and tetraamide, are isolated.

We claim:

1. A linear poly(amino acid) compound of formula

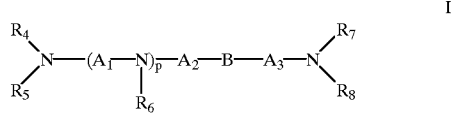

wherein $A_1$, $A_2$ and $A_3$, which are identical or different, represent

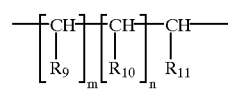

m and n being integers from 0 to 5, the sum of which has the value 1 to 5, $R_9$, $R_{10}$ and $R_{11}$ independently represent H, alkyl, alkoxy-alkyl, phenyl or phenylalkylene and $R_{10}$ additionally may represent OH or alkoxy, or one of the $R_9$ and $R_{11}$ groups from $A_1$, $A_2$ and $A_3$ represents the formula

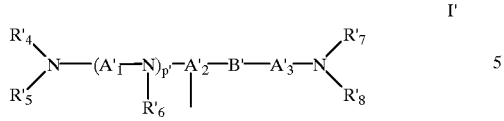     I' in which the letters can have the meanings of the letters with the same index number of the formula I, with the exception of one of the $R'_9$ and $R'_{11}$ groups which represents ($C_1$–$C_8$) alkylene, optionally substituted by one or more ($C_1$–$C_8$) alkoxy groups, the other not being I';

$R_4$, $R_5$, $R_6$, $R_7$ and $R_8$ independently represent H, alkyl, alkoxyalkyl, amidoalkyl, alkyl-substituted amidoalkyl, alkoxy-substituted amidoalkyl, or CH($R_{12}$)X, $R_{12}$ being H, alkyl, alkoxyalkyl or $R_1$;

X represents $CO_2R_3$, $CONR_bR_c$ or $P(Rd)O_2H$ and $R_a$, $R_b$ and $R_c$, which are identical or different, represent H or optionally hydroxylated ($C_1$–$C_8$)alkyl, Rd represents OH, ($C_1$–$C_8$)alkyl or ($C_1$–$C_8$)alkoxy;

$R_1$ represents a group having a molecular weight greater than 200 selected from the group consisting of polyoxy ($C_2$–$C_3$)alkylene moiety with a molecular weight less than 150,000, polyol moiety with a molecular weight less than 20,000, monofunctionalized oligosaccharide moiety of 2 to 10 units, monofunctionalized polysaccharide moiety with a molecular weight less than 20,000, and $R_2$—G—$R_3$ in which $R_2$ represents a covalent bond, alkylene, alkoxyalkylene, polyalkoxyalkylene, alkylene interrupted by phenylene, phenylene or a saturated or unsaturated heterocyclic moiety;

G represents an O, CO, OCO, COO, $SO_3$, $OSO_2$, CONR', NR'CO, NR'COO, OCONR', NR', NR'CS, CSNR', $SO_2NR'$, $NR'SO_2$, NR'CSO, OCSNR', NR'CSNR', P(O)(OH)NR' or NR'P(O)(OH) functional group, in which R' is H, ($C_1$–$C_8$)alkyl or $R_3$;

$R_3$ represents alkyl, phenyl, alkyl substituted or interrupted by one or more groups selected from the group consisting of phenyl, alkyleneoxy, amino, amido alkyl-substituted amino and alkyl-substituted amido wherein alkyl is optionally substituted or interrupted by one or more groups selected from the group consisting of phenyl, alkyleneoxy, amino, amido, alkyl-substituted amino and alkyl-substituted amido; or $R_3$ is selected from the group consisting of an optionally monofunctionalized saccharide, oligosaccharide, peptide, biocompatible natural and synthetic macromolecule selected from the group consisting of polyoxy($C_2$–$C_3$) alkylene, polyether, polysaccharide poly(amino acid), protein, glycoprotein, oligomer and starburst polymer, and a molecule, capable of binding to an endogenous bioreceptor moiety, selected from the group consisting of a hormone, prostaglandin, steroid, antibody, lipid, arabinogalactan, glucose and glycoprotein without sialic acid;

B is O or N—W and W represents the same as $R_5$ or polyoxy($C_2$–$C_3$)alkylene, ($C_1$–$C_6$)alkylene-Y or Y;

Y being a saturated or unsaturated heterocycle selected from the group consisting of thiophene, furan, pyran, pyrrole, pyrrolidine, morpholine, piperazine, imidazole, pyridine, pyrimidine, pyrazine, pyridazine, thiazole, oxazole, imidazoline, dioxan, tetrazole, benzofuran, indole, quinoline and more saturated and less saturated derivatives and isomers, thereof, said heterocycle being optionally substituted by one or several OH, alkyl, alkoxy or alkoxyalkyl groups, with the proviso that when W represents Y, the carbon bonded to N is bonded to 2 carbon atoms of the heterocycle, or W represents the formula

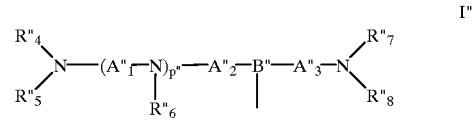     I"

in which the letters can have the meanings of the letters with the same index number in the formula I, with the exception of $R''_9$ and $R''_{11}$; which can not represent I' and of B" which represents N—Q, Q being ($C_1$–$C_8$)alkylene optionally substituted by one or more alkoxy groups, or $A_2$—B—$A_3$ represents a heterocyclic group in which B is a saturated or unsaturated heterocycle selected from thiophene, furan, pyran, pyrrole, pyrrolidine, morpholine, piperazine, imidazole, pyridine, pyrimidine, pyrazine, pyridazine, thiazole, oxazole, imidazoline, dioxan, tetrazole, and more and less saturated derivatives and isomers, thereof, $A_2$ and $A_3$ represent a group CH—$R_e$ in which $R_e$ is H or ($C_1$–$C_6$) alkyl, p is an integer from 0 to 5, it being understood that at least three substituents selected from $R_4$, $R_5$, $R_6$, $R_7$ and $R_8$ represent, CH($R_1$)X, wherein phenyl, phenylene and heterocyclic groups may be substituted by one or more OH, Cl, Br, I, ($C_1$–$C_8$) alkyl, ($C_1$–$C_8$)alkoxy, $NO_2NH_2$, $NR_xR_y$, $NR_xCOR_y$, $CONR_xR_y$ or $COOR_x$ groups, with $R_x$ and $R_y$ being H or ($C_1$–$C_8$)alkyl, and the alkyl, alkylene and alkoxy which may be optionally hydroxylated, are linear or branched, $C_1$ to $C_{14}$ groups, or a salt thereof.

2. The compound as claimed in claim 1, wherein X represents an acid functional group and $R_1$ represents $R_2$—G—$R_3$ and $R_2$ represents ($C_1$–$C_6$)alkylene, optionally interrupted by phenylene, G represents CONR', NR'CO or O, R' being H, ($C_1$–$C_8$)alkyl or $R_3$, and $R_3$ represents ($C_1$–$C_4$)alkyl optionally substituted or interrupted by one or more groups selected from the group consisting of phenyl, ($C_1$–$C_6$)alkoxy, alkyleneoxy, amino, amido, amino substituted by alkyl or alkoxy-alkyl, amido substituted by alkyl or alkoxy-alkyl, an optionally monofunctionalized saccharide, oligosaccharide, peptide and biocompatible macromolecule moiety, and $R_2$, R' and $R_3$ groups may additionally be hydroxylated.

3. The compound as claimed in claim 1, containing 4 groups CH($R_1$)X.

4. The compound as claimed in claim 1, wherein the groups CH($R_1$)X are identical.

5. A compound according to claim 1, of formula

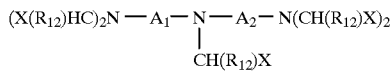
III in which $A_1$ and $A_2$ independently represent

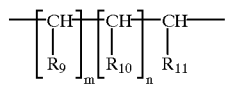

m and n being 0, 1 or 2 and their sum having the value 1 or 2, $R_9$, $R_{10}$ and $R_{11}$ independently representing H, alkyl, alkoxyalkyl, phenyl or phenylalkylene, and $R_{10}$ may additionally represent OH or alkoxy, or one of the $R_9$ and $R_{11}$ groups represent the formula

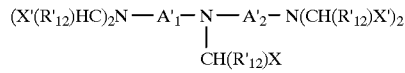
III' in which the letters can have the meanings of the letters with the same index number of the formula III, with the exception of $R'_9$ and $R'_{11}$, which can not represent III' and one of which represents $(C_1-C_8)$alkylene, optionally carrying one or more alkoxy groups, $R_{12}$ represents H, alkyl, alkoxyalkyl or $R_1$, X and $R_1$ being as defined in claim 1, or a salt thereof.

6. The compound of formula I according to claim 1, wherein $A_1$, $A_2$, $A_3$, B, p, $R_4$, $R_5$, $R_6$, $R_7$ and $R_8$ are as defined in claim 1, with the exception of 3 groups from $R_4$, $R_5$, $R_6$, $R_7$ and $R_8$ which represent $CH(R_2-G')X'$; X' representing optionally protected X, $R_2$ and X being as defined in claim 1, and G' representing a reactive functional group such as COOR', $SO_3R'$, $PO_3R'$, NHR', $SO_2NHR'$, N=C=S, N=C=O or OH, R' being H or $(C_1-C_8)$-alkyl, or a salt or metal cation thereof.

7. The compound of formula III according to claim 5 comprising at least three $CH(R_{12})X$ groups in which $R_{12}$ is selected from the group consisting of $R_1$, H, alkyl and alkoxyalkyl and X is —COOH.

8. A chelate formed between a paramagnetic metal ion and a compound as claimed in claim 1.

9. The chelate according to claim 8, in which the ion is that of gadolinium or manganese.

10. A composition for medical imaging by nuclear magnetic resonance, comprising a chelate as claimed in claim 8 and a physiologically acceptable vehicle.

* * * * *